United States Patent [19]

Smith

[11] Patent Number: 5,092,893
[45] Date of Patent: Mar. 3, 1992

[54] HUMAN ORTHOPEDIC VERTEBRA IMPLANT

[76] Inventor: Thomas E. Smith, 388 Staghorn, Wright City, Mo. 63390

[21] Appl. No.: 577,148

[22] Filed: Sep. 4, 1990

[51] Int. Cl.⁵ ............................................. A61F 2/00
[52] U.S. Cl. ...................................... 623/17; 606/60; 606/61
[58] Field of Search .............. 623/17, 20, 66; 606/60, 606/61; 128/69

[56] References Cited

U.S. PATENT DOCUMENTS

| | | | |
|---|---|---|---|
| 3,693,616 | 9/1972 | Roaf et al. ............................ | 606/61 |
| 4,003,376 | 1/1977 | McKay et al. ........................ | 606/61 |
| 4,448,191 | 5/1984 | Rodnyansky et al. ................ | 606/61 |
| 4,759,769 | 7/1988 | Hedman et al. ....................... | 623/17 |
| 4,836,196 | 6/1989 | Park et al. ............................. | 606/61 |
| 4,946,458 | 8/1990 | Harms et al. ......................... | 623/17 |

FOREIGN PATENT DOCUMENTS

| | | | |
|---|---|---|---|
| 303773 | 5/1988 | European Pat. Off. . | |
| 0340160 | 11/1989 | European Pat. Off. ............ | 606/61 |
| 3729600 | 3/1989 | Fed. Rep. of Germany ........ | 623/17 |
| 2612070 | 9/1988 | France ................................... | 606/61 |
| 923532 | 5/1982 | U.S.S.R. . | |
| 1179984 | 9/1985 | U.S.S.R. ............................... | 606/61 |

*Primary Examiner*—David J. Isabella
*Attorney, Agent, or Firm*—Gravely, Lieder & Woodruff

[57] ABSTRACT

A vertebra structural implant for connecting two or more vertebral bodies in axial and lateral directions having implant plates attached to opposed sides of the spinal column by studs with a cross brace between the implant plates to prevent slipping or rotating of the vertebrae being stabilized. The implant has openings with curved lips and the studs have spherical surfaces and fit freely through the openings to prevent angular misalignment between the studs and the plates to lessen stress on the studs. The implant has grooved lock washers and the cross brace has grooves which mate with grooves in the implant plates to lock the plates in position relative to the studs and to each other.

16 Claims, 2 Drawing Sheets

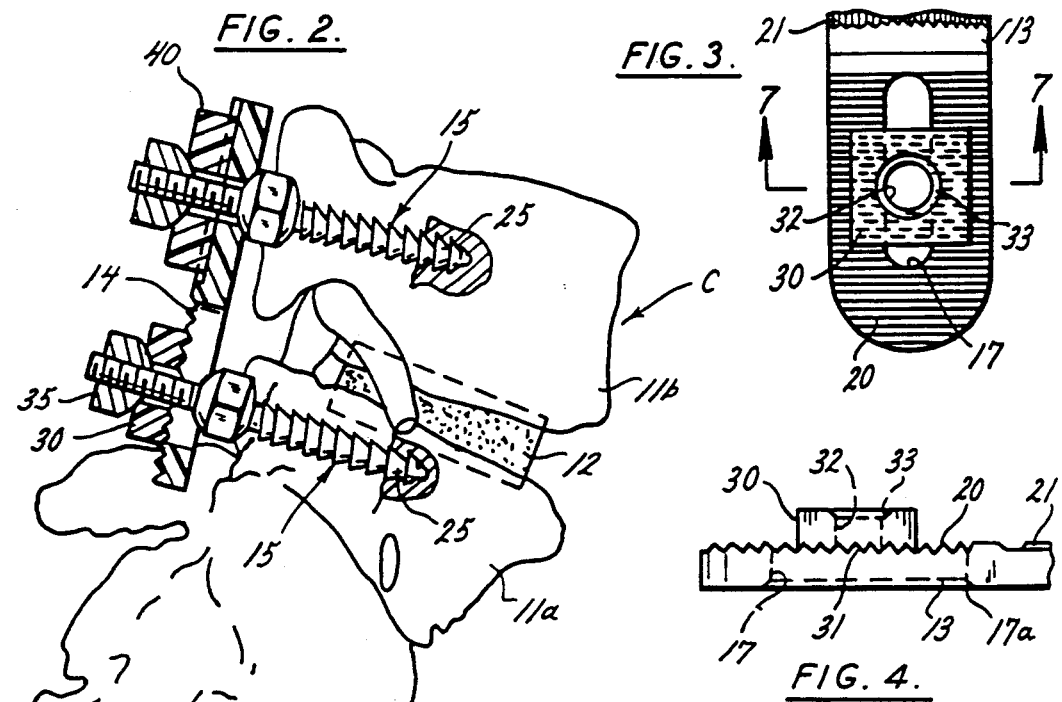
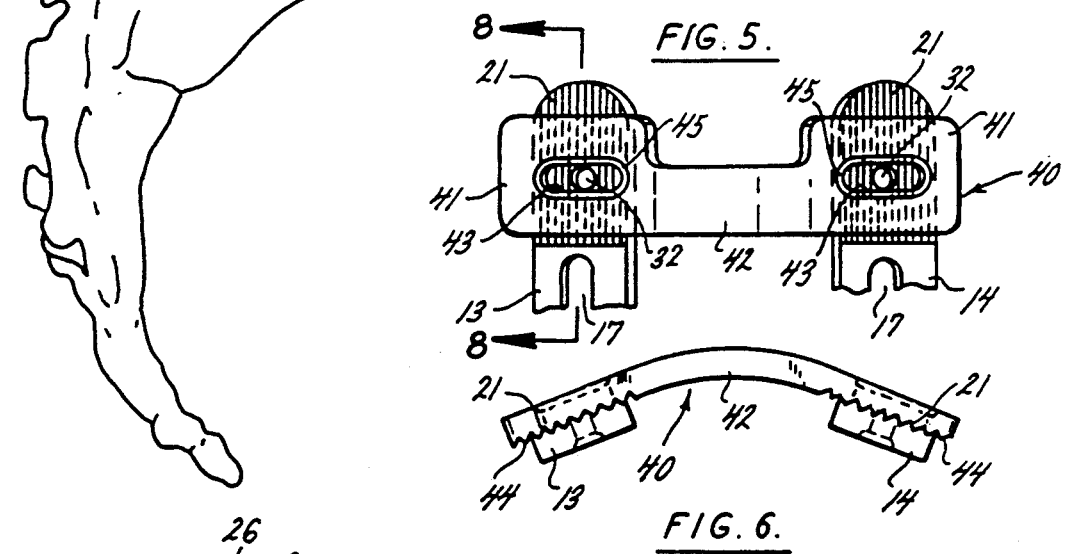
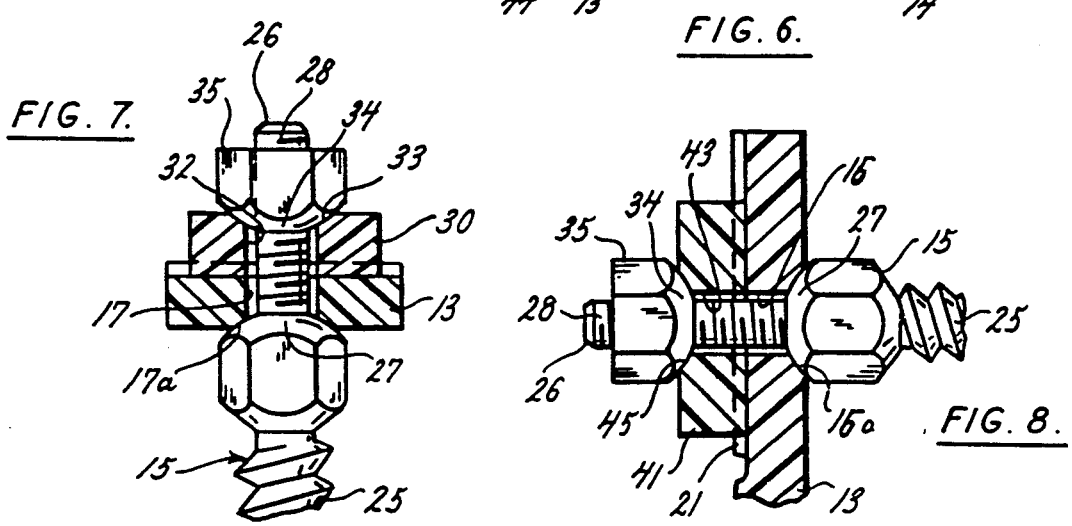

HUMAN ORTHOPEDIC VERTEBRA IMPLANT

BACKGROUND OF THE INVENTION

1. Field of the Invention

The present invention relates to the correction of spinal columns, and in particular the present invention relates to a surgically implantable device for maintaining vertebral bodies of the spinal column in a desired relationship during healing of a portion of the spinal column.

2. Description of the Prior Art

Surgery is required to correct deformation or degeneration or damage to a human spinal column, and in certain procedures at least one of the intervertebral discs is removed from a damaged portion of the spinal column. Bone graft is prepared, which may include the patient's bone or bone from another source. The bone graft is placed in the position from which the damaged disc has been removed. At this point it is necessary to fix the relation of the vertebral bodies on each side of the bone graft to maintain the vertebral bodies in a desired relationship and to prevent load from being transmitted through the bone graft while it is fusing.

It is desired that there be axial adjustment of the implant plates to account for differences between various vertebrae and the positioning of the screws or studs which are threaded into the vertebrae. It is important that these plates be accurately located and maintained in fixed position with respect to the studs.

It is also desirable that the implant plates on each side of the spinal column be cross braced with relatively rigid curved cross braces to maintain the lateral alignment of the vertebrae during the fusion process.

A further desirable attribute of a vertebral implant is that there be an adjustment for angular misalignment of the studs and the implant plates at the time the studs are threaded into the vertebrae. This allows for a correction in the amount of stress that is on the implant after it is tightened together. If an implant is highly stressed when it is placed into position, it is not an uncommon occurance that a stud will break at the stress point. This of course is undesirable in the healing process and requires a second operation to replace the broken screw.

Accordingly, it is a principal object of the present invention to provide a vertebra structural implant for connecting two or more vertebral bodies in axial and lateral directions whereby healing of a bone graft between the vertebral bodies is enhanced.

It is a further object of the present invention to provide a vertebral structural implant in which there is a lateral cross brace between the longitudinally positioned implant plates placed along the vertebrae being fixed together.

Still another object is to provide means for compensating for angular misalignment between the stud and the implant plate to reduce stress on the stud when it is firmly fastened to the implant plate.

Still another object is to provide a vertebra structural implant which has axial adjustment between an implant plate and studs fixed to adjacent vertebrae between which a bone graft has been placed with means for locking the parts together in close axial alignment along with means for compensating for angular misalignment between the studs and the implant plate to reduce stress on the studs.

These and other objects and advantages will become apparent hereinafter.

SUMMARY OF THE INVENTION

The present invention comprises a vertebra structural implant for rigidly connecting vertebral bodies in axial and lateral directions in the spinal column when bone graft is located between the vertebral bodies. The implant comprises a pair of laterally spaced longitudinal implant plates which are axially adjustably connected to the adjacent vertebrae by attaching studs fixed in the vertebrae. The implant also includes laterally adjustable cross braces to maintain the implant plates in fixed lateral position and means for compensating for angular misalignment between the studs and the attaching implant plates to reduce stress on the studs when the device is implanted.

BRIEF DESCRIPTION OF THE DRAWINGS

Further features of the present invention will become apparent to those skilled in the art to which the present invention relates from reading the following specifications with reference to the accompanying drawings in which like numbers refer to like parts wherever they occur

FIG. 2 is a fragmentary side elevational view partly in section of the structure shown in FIG. 1;

FIG. 3 is a fragmentary plan view of the implant plate and axial adjustment nut without the attachment stud or lock nut;

FIG. 4 is a fragmentary side elevational view of the structure shown in FIG. 3;

FIG. 5 is a fragmentary plan view showing the cross brace in position without the attachment stud or lock nut;

FIG. 6 is a fragmentary side elevational view partly in section of the structure shown in FIG. 5;

FIG. 7 is an enlarged fragmentary sectional view taken along line 7—7 of FIG. 3 showing the arrangement which compensates for angular misalignment between the stud and the implant plate and showing the lock nut and the axial adjustment nut;

FIG. 8 is an enlarged fragmentary sectional view taken along line 8—8 of FIG. 5 and showing the locking arrangement which compensates for angular misalignment between the stud, the implant plate and the cross brace;

DETAILED DESCRIPTION

Figure 1:
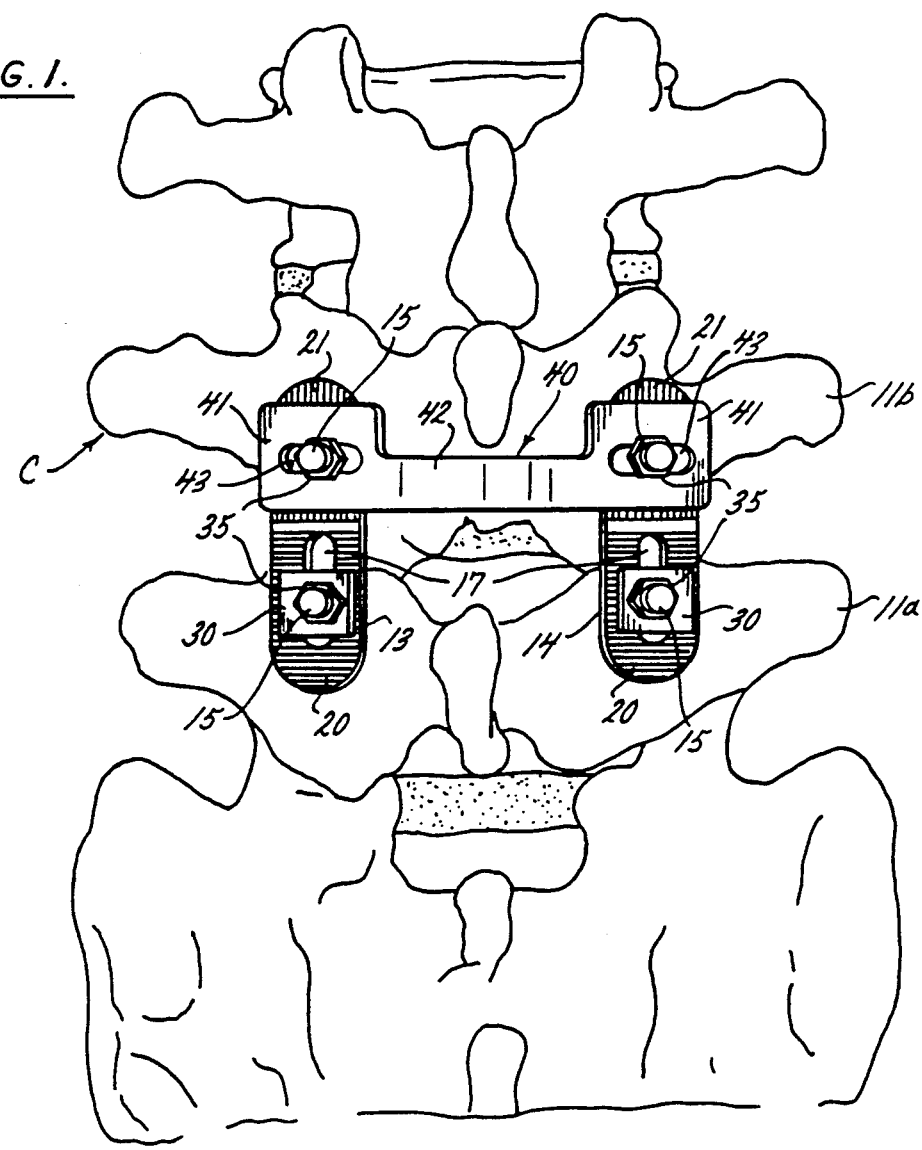
FIG. 1 is a fragmentary plan view of the present device installed in a human spinal column.
Figure 9:
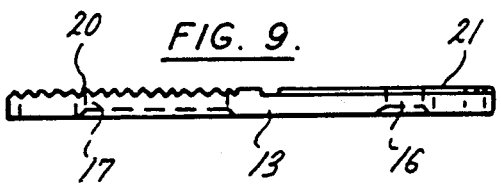
FIG. 9 is a detailed side view of the implant plate.
Figure 11:
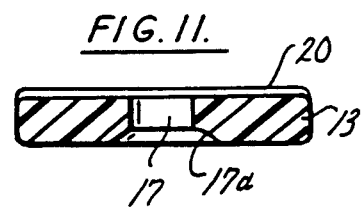
FIG. 11 is a sectional view taken along line 11—11 of FIG. 10.

The apparatus shown in FIGS. 1 & 2 comprises a vertebra structural implant assembly 10 which is positioned on a human spinal column "C" between adjacent vertebrae 11a and 11b. The disc material has been removed from between the vertebrae 11a and 11b and replaced by a bone implant or bone block 12 using the patient's own bone taken from the hip or bone from a bone bank. These bone blocks, or grafts, eventually grow together, or fuse, and in doing so entirely eliminate the movement of this section of the spine, thus removing one of the causes of back and leg pain.

These bones fuse into a solid mass in about six months under normal conditions.

In order to insure that this work will give lasting relief from back and leg pain, spine plates are used to stabilize the back in the best possible position. Achieving spinal fusion in an unstable or misaligned spine without spine plates is very difficult because there is nothing to prevent the spine from moving while the bone between the vertebra is fusing.

Fusion progresses best when the spine is rigid and the bone grafts are kept compressed under constant pressure. In order to decrease motion in the spine and in order to add rigidity to the spine, spine plates are attached to the spinal column.

The structural spine implant assembly 10 comprises a pair of implant plates 13 and 14 which are axially positioned on each side of the spinal column "C". The implant plates 13,14 are held in position by means of threaded studs 15 which are fixed into the vertebrae 11a,11b.

The implant plates 13,14 are axially elongated and have laterally opposed sets of circular openings 16 adjacent to one end and laterally opposed sets of elongated slots 17 adjacent to the other end. The undersides of the implant plates 13,14 at the openings 16 and the undersides of the implant plates 13,14 at the openings 17 are cut in a 360° curvature to define the curved surfaces 16a and 17a respectively. In effect the surfaces 16a at the circular openings 16 are spherical bearing surfaces and the curved surfaces 17a along the elongated slots 17 are cylindrical surfaces as seen along the axis of the plates 13,14 and spherical surfaces around the ends of the slots 17 (see FIGS. 9-12).

The top surfaces of the plates 13,14 adjacent to the elongated slots 17 have lateral serrations or grooves 20 which, in effect, define a plurality of horizontal or lateral peaks and valleys extending transversely across the plates 13,14 at the ends of the plates 13,14 having the elongated openings 17 (FIGS. 1, 3, 4). The implant plates 13,14 also have a similar series of serrations or grooves 21 adjacent to the circular openings 16 but, these serrations 21 run axially or longitudinally along the plates 13,14 about the circular openings 16 (FIGS. 1, 5, 6).

The attachment studs 15 have threaded ends 25 (FIG. 2) which are screwed into openings drilled into the vertebrae 11a,11b to attach said studs 15 to the vertebrae 11a,11b. The opposite or free ends 26 of the studs 15 begin in spherical bearing surfaces or shoulders 27 (FIGS. 7, 8) where the anchor threads 25 end and before the attachment threads 28 begin. These shoulders are designed to mate with the bearing surfaces 16a and 17a so as to anchor the plates 13,14 to the studs 15.

Substantially square lock washers 30 having serrated lateral serrations or grooves 31 along their under surfaces are designed to mate with the lateral serrations 20 on the implant plates 13,14. The bearing or lock washers have circular center openings 32 adapted to loosely receive the threaded ends 28 of the studs 15 (FIG. 7). The lips 33 which surround the bearing washer central openings 32 have the shape of spherical counterbores which are designed to mate with a spherical surface or shoulder 34 on lock nuts 35.

Axial Adjustment

The serrations 31 on the lock or bearing washers 30 match the lateral serrations 20 on the implant plates 13,14 and, in combination with the fixed position of the end of the bearing plates 13,14 which contain the circular openings 16, provide for incremental axial adjustment of the plates 13,14 to allow close axial alignment of the studs 15 and the plates 13,14. The serrations 20,31 are about 0.02 to about 0.03 inches deep and about 0.02 inches from peak to peak. This provides a stud adjustment capability of about ±0.01 inches.

The locking of the washers 30 to the plates 13,14 through engagement of the serrations 20,31 prevents relative movement between the studs 15 and stabilizes the vertebrae into which the studs 15 are fixed. Misalignment between the attaching studs 15 and the implant plates 13,14 cause a corresponding misalignment to occur between the vertebrae being stabilized by the implant. This results in deformity of the spinal column or stress on the bone being fused.

Angular Misalignment Compensation

I use a technique of spherical surfaces and cylindrical or spherical surfaces of mating parts to provide compensation for angular misalignment between the attaching studs and the implant plate. Spherical surfaces on both the attaching studs and locking nuts mate with either a cylindrical or spherical surface on the implant plates and with spherical surfaces on the bearing washers. This arrangement allows the studs to be installed and secured at an angle to the implant plates without bending the studs.

Presently used plate/stud designs force the plates and studs to be at a 90° angle to each other when the locking nut is tightened. This is due to both the nut and screw interfacing with the same part, i.e. the plate, with no means of relative displacement between the interfacing surfaces to allow for angular misalignment. Thus, existing designs must be perfectly aligned or bending of the studs will occur when the nuts securing the assembly are tightened. This bending prestresses the studs and can lead to failure of the studs.

Specifically, the arrangement of the curved bearing surfaces 16a,17a, and the wide implant plate openings 16,17, in combination with the curved lock washer bearing surfaces 33 and the wide lock washer openings 32 provide means for compensation for axial misalignment of the studs 15 with respect to the implant plates 13,14. The lock nuts 35 have spherical engagement shoulders 34 and the anchor screws 25 also have spherical engagement shoulders 27.

Figure 10:
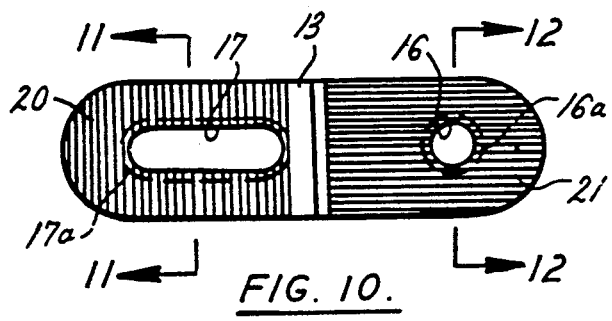
FIG. 10 is a plan view of the implant plate.
Figure 12:
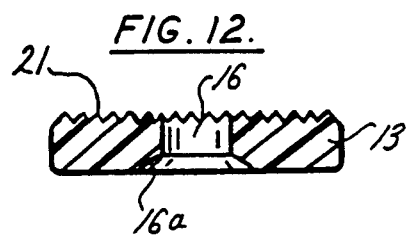
FIG. 12 is a sectional view taken along line 12—12 of FIG. 10.

The implant plate ends which contain the circular openings 16 also have spherical lips 16a on the undersides of the openings 16. These mate with the spherical shoulders 27 on the studs 15. The spherical ends 34 of the lock nuts 35 mate with the cylindrical surfaces 45 of the cross brace 40 (FIGS. 8, 10, 12).

As the studs 15 are not positioned precisely at right angles to the vertebrae 11a,11b, this arrangement of curved mating surfaces and openings larger than the stud body allows angular adjustment of the implant plates 13,14 with respect to the studs 15 while still providing for a rigid connection therebetween to stabilize the vertebrae. Preferably, there is about 0.02 to about 0.03 inches between the sides of the stud shanks 28 and the insides of the openings 16,17,32.

Implant Cross Brace

It is often desirable to link the adjacent implant plates 13,14 laterally across the spinal column "C". This further rigidifies the structure of the implant. To do this, I provide curved cross braces 40 which cooperate with the implant plates 13,14 and are connected to them at the area of the circular openings 16.

On the tops of the implant plates 13,14 are the longitudinal serrations or grooves 21 which extend horizontally along the plate upper surfaces in the area of the circular opening 16.

The cross brace 40, which has enlarged end portions 41 and a curved center section 42, is provided with elongated slots 43 in the end portions 41 to accommodate the threaded free ends 28 of the studs 15 (FIGS. 5,6). The openings 43 are wider than the diameter of the threaded stud sections 28. The underside of the cross brace 40 in the vicinity of the slots 43 has transverse serrations 44 similar to the serrations 21 in the implant plates 13,14. These sets of serrations 44 and 21 are designed to mate and tightly lock the cross piece 40 to the implant plates 13,14. The upper lips 45 of the cross brace slots 43 are curved in a cylindrical fashion, again taken along the axis of the cross brace 40. These lips 45 are designed to mate with the spherical shoulders 34 on the lock nuts 35 and provide accommodation for angular misalignment of the studs 15 with respect to the implant plates 13,14 and the cross braces 40 (FIG. 8).

While the drawings show implant plates connecting two vertebrae, more than two vertebrae may be positioned by the invention depending on the length of the implant plates and the number of studs used.

This invention is intended to cover all changes and modifications of the example of the invention herein chosen for purposes of the disclosure which do not constitute departures from the spirit and scope of the invention.

What is claimed is:

1. A vertebra structural implant for connecting two or more vertebral bodies in axial and lateral directions in a spinal column, the implant comprising:
   (a) a pair of implant plates adapted for attachment to adjacent vertebrae on opposite sides of the spinal column, each of the plates having an underside surface adapted to generally face the vertebrae, and a top surface adapted to generally face away from the vertebrae, and corresponding axially spaced mountings openings extending therethrough, the mounting openings in each plate being positionable on opposite sides of the spinal column to form at least first and second sets of laterally opposed mounting openings;
   (b) an attaching stud for each mounting opening, each attaching stud having a first end adapted for attachment to a vertebral body, and a second end adapted to extend through and be secured within one of the mounting openings in one of the plates;
   (c) axial adjustment means for providing axial adjustment between the plates and their respective attaching studs in adjacent vertebrae;
   (d) securing means associated with at least one of the sets of mounting openings for securing the second ends of the attaching studs within the mounting openings to prevent relative movement between the plates and their respective attaching studs;
   (e) a lateral cross brace having first and second ends and adapted to extend beween the plates and
   (f) locking means associated with the lateral cross brace and the mounting openings of one of the sets of mounting openings for locking each end of the cross brace in a fixed position relative to one of the implant plates, to prevent slipping or rotating of the vertebrae being stabilized.

2. The structure of claim 1 wherein the axial adjustment means comprises the mounting openings of at least one of the sets of mounting openings being axially extending slots; and wherein the securing means comprises laterally extending grooves in the top surface of each implant plate, adjacent to the axial slot, a lock washer having corresponding laterally extending grooves adapted to lock into the laterally extending grooves in each implant plate, and an opening to accommodate the second end of the attaching stud; and a lock nut adapted to be secured on the second end of each attaching stud to lock the implant plate and the attaching stud against relative axial movement when the lock nut is tightened against the lock washer.

3. The structure of claim 2 wherein the laterally extending grooves in the implant plates and the lock washers are about 0.02 to about 0.03 inches deep and about 0.02 inches from peak to peak.

4. The structure of claim 3 wherein the mounting openings of the first set are axially extending slots and wherein the mounting openings of the second set are generally circular.

5. The structure of claim 1 wherein the locking means comprises axially extending grooves in the top surface of each implant plate, adjacent the mounting opening of the associated set; corresponding axially extending grooves in each end of the lateral cross brace adapted to lock into the axially extending grooves in the implant plates, and a lock nut adapted to be secured on the second end of the attaching stud extending through each of the mounting openings to lock each end of the cross brace to its respective implant plate when the lock nut is tightened down on the cross brace.

6. The structure of claim 5 wherein the axially extending grooves in the implant plates and the lateral cross brace are about 0.02 to about 0.03 inches deep and about 0.02 inches from peak to peak.

7. A vertebra structural implant for stabilizing adjacent vertebral bodies in a spinal column, the implant comprising:
   (a) a pair of implant plates adapted for attachment to adjacent vertebrae on opposite sides of the spinal column, each of the plates having an underside surface adapted to generally face the vertebrae, and a top surface adapted to generally face away from the vertebrae, and corresponding axially spaced mounting openings extending therethrough, the mounting openings on each plate being positionable on opposite sides of the spinal column to form at least first and second sets of laterally opposed mounting openings, the openings at the underside surface being rounded;
   (b) an attaching stud for each mounting opening, each attaching stud having a first end adapted for attachment to a vertebral body, and a second end adapted to extend through, and be secured within, one of the mounting openings in one of the implant plates;
   (c) axial adjustment means for providing axial adjustment between the plates and their respective attaching studs in adjacent vertebrae;
   (d) securing means associated with at least one of the sets of mounting openings for securing the second ends of the attaching studs within the mounting openings to prevent relative movement between the plates and their respective attaching studs; and
   (e) alignment means to compensate for angular misalignment between the attaching studs and the implant plates to reduce stress on the studs when the studs are fastened to the plates, said means comprising rounded surfaces on the second end of the studs matable with the rounded openings in the underside of the implant plates, and means connecting the securing means and the top surface of the implant plates to allow movement of the plate with respect to the stud in all directions before the securing means secures the stud to the implant plate.

8. The structure of claim 7 wherein the axial adjustment means comprises the mounting openings of at least one of sets of mounting openings being axially extending slots; and wherein the securing means and the means connecting the implant plates to the securing means comprises laterally extending grooves in the top surface of each implant plate, adjacent to the axial slots; a lock washer having corresponding laterally extending grooves adapted to lock into the laterally extending grooves in each implant plate, and an opening to accommodate the second end of the attaching stud; and a lock nut adapted to be secured on the second end of each attaching stud to lock the implant plate against relative axial movement when the lock nut is tightened against the lock washer.

9. The structure of claim 8 wherein the laterally extending grooves in the implant plates and the lock washers are about 0.02 to about 0.03 inches deep and about 0.02 inches from peak to peak.

10. The structure of claim 9 wherein the mounting openings of the first set comprise axially extending slots and wherein the mounting openings of the second set are generally circular.

11. The strucutre of claim 8 wherein the mounting openings in the implant plates and the openings in the lock washers though which the second ends of the studs pass are larger than the second ends of the studs so that the studs are angularly adjustable with respect to the implant plates; and including rounded mating bearing surfaces between the second ends of at least some of the studs and the underside surfaces of the plates, and between the lock nuts and lock washers whereby misalignment between the studs and the implant plates is compensated.

12. A vertebra structural implant for connecting two or more vertebral bodies in axial and lateral directions in a spinal column, the implant comprising:
  (a) a pair of implant plates adapted for attachment to adjacent vertebrae on opposite sides of the spinal column, each of the plates having an underside surface adapted to generally face the vertebrae, and a top surface adapted to generally face away from the vertebrae and corresponding axially spaced mounting openings extending therethrough, the mounting openings in each plate being laterally alignable with the mounting openings on the other plate when the plates are positioned on opposite sides of the spinal column to form at least first and second sets of laterally opposed mounting openings:
  (b) an attaching stud for each mounting opening, each stud having a first end adapted for attachment to a vertebral body, and a second end adapted to extend through and be secured within one of the mounting openings in one of the implant plates;
  (c) axial adjustment means for providing axial adjustment between the plates and their respective attaching studs in adjacent vertebrae;
  (d) securing means associated with at least one of the sets of mounting openings for securing the second ends of the attaching studs within the mounting openings to prevent relative movement between the plates and their respective attaching studs;
  (e) a lateral cross brace having first and second ends and adapted to extend between the plates;
  (f) locking means associated with the lateral cross brace and the mounting openings of one of the sets of mounting openings for locking each end of the cross brace in a fixed position relative to one of the implant plates, to prevent slipping or rotating of the vertebrae being stabilized; and
  (g) alignment means to compensate for angular misalignment between the attaching studs and the associated implant plates to reduce stress on the studs when the studs are fastened to the plates.

13. The structure of claim 12 wherein the axial adjustment means comprises the mounting openings of at least one of the sets of mounting openings being axially extending slots; and wherein there are laterally extending grooves in the top surface of each implant plate, adjacent to the axial slots; and lock washer having corresponding laterally extending grooves adapted to lock into the laterally extending grooves in each implant plate, the and an opening to accommodate the second end of the attaching stud; and lock nut adapted to be secured on the second end of each attaching stud to lock the implant plate against relative axial movement when the lock nut is tightened against the lock washer.

14. The structure of claim 13 wherein the locking means comprises axially extending grooves in the top surface of each implant plate, adjacent the mounting openings of the associated set; corresponding axially excluding grooves in each of the lateral cross brace adapted to lock into the axially extending grooves in the implant plates, and a lock nut adapted to be secured on the second end of the attaching stud to lock the cross brace to its respective implant plate when the lock nut is tightened down on the cross brace.

15. The structure of claim 14 wherein the mounting openings in the implant plates and the openings in the lock washers through which the second ends of the studs pass are larger than the second ends of so that the studs are angularly adjustable with respect to the implant plates; and including rounded mating bearing surfaces between the second ends of at least some of the studs and the underside surfaces of the plates, and between the lock nuts and lock washers, whereby angular misalignment between the studs and the plates is compensated.

16. A vertebra structural implant for connecting vertebral bodies in axial and lateral directions in a spinal column, the implant comprising:
  (a) a pair of implant plates adapted for attachment to adjacent vertebrae on opposite sides of the spinal column, each of the plates having an underside surface adapted to generally face the vertebrae, and a top surface adapted to generally face away from the vertebrae, and corresponding axially spaced mounting openings extending therethrough, the mounting openings in each plate being laterally alignable with the mounting openings on the other plate when the plates are positioned on opposite sides of the spinal column to form at least first and second sets of laterally opposed mounting openings, the openings of the first set of said openings being axially elongated slots and being surrounded by a curved bearing surface on the underside of the implant plate and the openings of the second set of said openings being circular and being surrounded by a curved bearing surface on the underside of the implant plate;

(b) an attaching stud for each mounting opening, each stud having a first end adapted for attachment to a vertebral body, and a second end adapted to extend through, and be secured within, one of the mounting openings in one of the implant plates, the second stud end being threaded and smaller than the elongated slots and circular openings to allow for angular adjustment therebetween, each of the studs further comprising a curved bearing surface to mate with one of the curved bearing surfaces on the underside of the implant plates;

(c) a series of laterally extending serrations along the top surfaces of the plates, adjacent the openings of the first set of openings and a series of axially extending serrations along the top surface of the plates adjacent the second set of openings;

(d) lock washers having underside surfaces adapted to generally face the top surface of an implant plates, and an upper surface adapted to generally face away from the implant plates, each lock washer having serrations on its underside surface adapted to mate with the laterally extending serrations on the implant plate, and and an opening therethrough sized to loosely accommodate the second end of one of the studs, the openings being surrounded by a curved bearing surface on the upper surface of the washer;

(e) lock nuts having a curved bearing surface adapted to mate with the curved bearing surface on the lock washer; and (f) a lateral cross brace having first and second ends, and being adapted to extend between the plates, set of plate openings, the cross brace having first and second ends adapted to be mounted at one of the openings of the second set of mounting openings, the cross brace having elongated slots in its end portions, said slots being wider than the second ends of the studs to receive the second end of the stud therein; the ends of the cross brace having serrations adapted to mate with the axially extending serrations in the plates, the slots in the ends of the lateral cross brace being surrounded by a curved bearing surface on the upper surface of the cross brace, and lock nuts having a curved bearing surface adapted to mate with the curved bearing surface on the cross brace to lock the cross brace in fixed position relative to the implant plates, said cross brace interconnecting the implant plates to prevent slipping or rotating of the vertebrae being stabilized;

(g) said combination of slots and loosely fitting studs with the curved bearing surfaces compensating for angular misalignment between the attaching studs and the associated implant plates to reduce stress on the studs when the studs are fastened to the plates by the lock nuts.

* * * * *